United States Patent [19]

Mancini

[11] Patent Number: 5,176,659
[45] Date of Patent: Jan. 5, 1993

[54] EXPANDABLE INTRAVENOUS CATHETER AND METHOD OF USING

[76] Inventor: Mario Mancini, 214½ E. Broad St., Quakertown, Pa. 18951

[21] Appl. No.: 662,404

[22] Filed: Feb. 28, 1991

[51] Int. Cl.⁵ ............................................. A61M 25/00
[52] U.S. Cl. ................................. 604/280; 604/164; 604/256
[58] Field of Search ............... 604/158, 159, 164, 165, 604/280, 264, 104, 281

[56] References Cited

U.S. PATENT DOCUMENTS

| | | | |
|---|---|---|---|
| 4,204,328 | 5/1980 | Kutner | 604/256 |
| 4,228,802 | 10/1980 | Trott | |
| 4,245,635 | 1/1981 | Kontos | |
| 4,601,713 | 7/1986 | Fuqua | 604/280 |
| 4,716,901 | 1/1988 | Jackson et al. | |
| 4,738,666 | 4/1988 | Fuqua | 604/104 |
| 4,795,426 | 1/1989 | Jones | 604/256 |
| 4,921,479 | 5/1990 | Grayzel | 604/280 |
| 5,015,329 | 5/1991 | Browne | 604/164 |

Primary Examiner—Gene Mancene
Assistant Examiner—Frank A. LaViola
Attorney, Agent, or Firm—Ferrill, Logan, Johns & Blasko

[57] ABSTRACT

The present invention provides an improved intravenous catheter which can be installed at a minimal diameter and expanded once installed to a full operational diameter. The apparatus of the present invention comprises a first catheter tube member with an expandable sidewall and a wider second member which inserts into the first member once the first member is installed in a vein to cause it to expand to an operational diameter. The apparatus and method of the present invention provide many options to medical personnel and are particularly useful when employed in trauma situations.

13 Claims, 4 Drawing Sheets

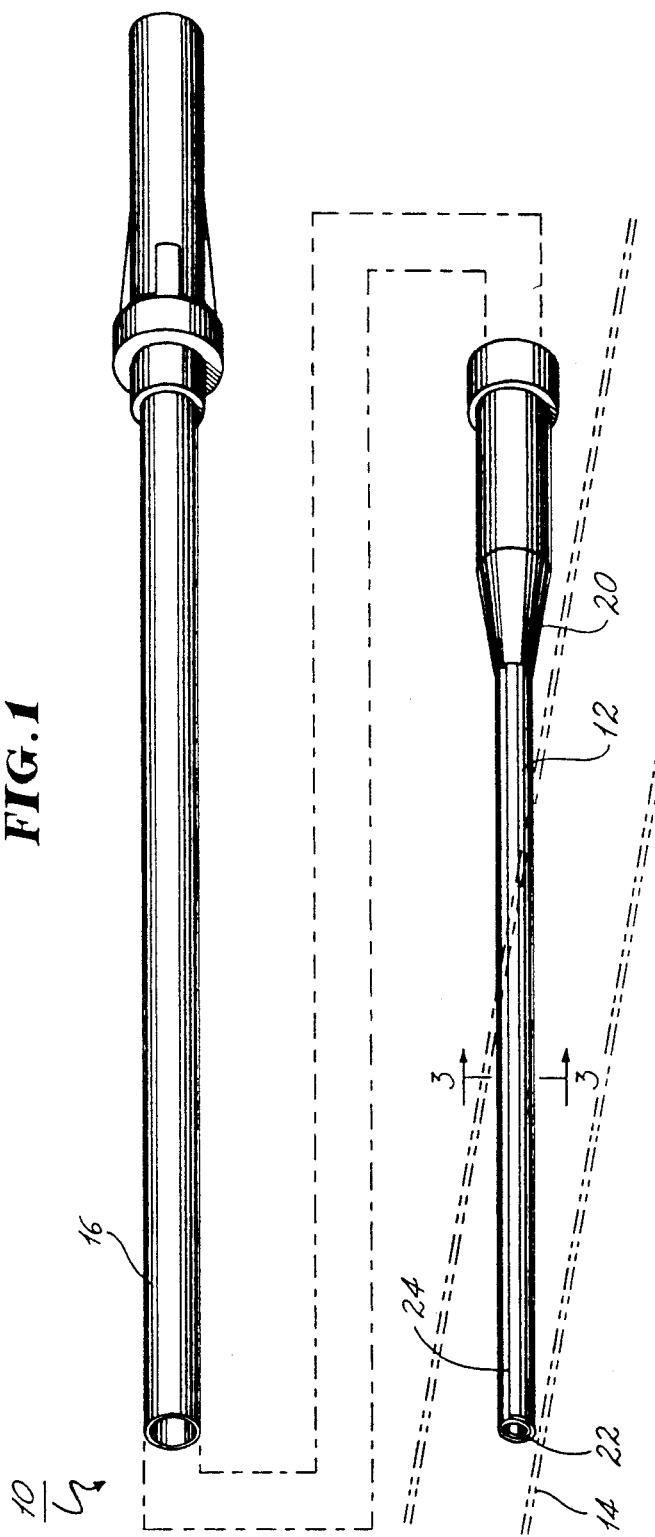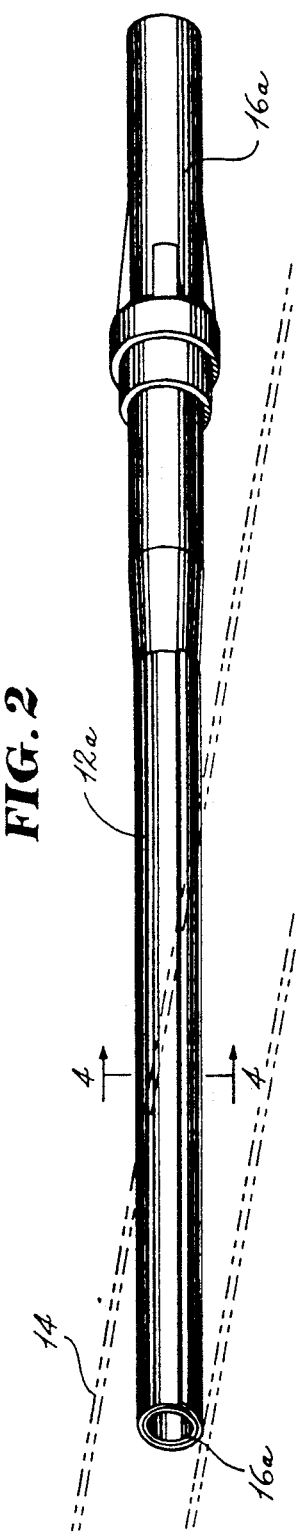

EXPANDABLE INTRAVENOUS CATHETER AND METHOD OF USING

BACKGROUND OF THE INVENTION

1. Field of the Invention

The present invention relates to catheters for delivering fluids intravenously to a patient. In particular, the present invention provides an improved catheter which can be expanded once inserted so to provide ease in insertion while permitting greater fluid flow during operation.

2. Description of the Prior Art

One major problem facing emergency medical personnel is that in times of trauma the circulatory system of a patient will contract to reduce blood flow. As a result, it is often very difficult to insert a catheter intravenously to provide necessary medication to the patient. Medical personnel are often forced to use a catheter of much smaller gauge than is necessary in order to be able to insert it into a contracted vein. This limits the amount of medication which can be delivered to the patient and complicates an already serious situation. Alternatively, medical personnel may have to make repeated attempts to insert a larger catheter tube, with resulting delay in providing medication and possible damage to the patient's skin and veins.

Although it has been suggested to employ expandable drainage tubes for other medical procedures, such a concept has not been applied to increase the fluid carrying capacity of an intravenous catheter once inserted. In U.S. Pat. No. 4,716,901 issued to Jackson et al. an expandable trocar is disclosed to introduce exploratory instruments or to drain a body cavity. This device is large, unwieldy and completely unsuitable for use in the delicate environment of intravenous catheterization. U.S. Pat. No. 4,228,802 issued to Trott discloses an expansion means to hold a drainage catheter in place in a bladder. Not only is the expansion means of this device unrelated to providing increased fluid carrying capacity, but, again, this device is unsuitable for use in an intravenous system. In U.S. Pat. No. 4,245,635 issued to Kontos an intravenous catheter is disclosed including valving to reduce or cease the flow through the catheter. This patent provides no teaching or suggestion that it may be beneficial to increase the size and fluid carrying capacity of the catheter once it is installed.

It is accordingly a primary object of the present invention to provide an intravenous catheter which may be readily inserted at a minimum contracted diameter and which may be expanded in size to increase its fluid carrying capacity once installed.

It is a further object of the present invention to provide such an intravenous catheter which includes means to maintain the catheter at its expanded size once installed.

It is an additional object of the present invention to provide such an intravenous catheter which integrates with existing medical apparatus and techniques and requires minimum training and time to install and use.

It is another object of the present invention to provide such an intravenous catheter which is of relatively simple construction and which can be manufactured at minimal additional expense.

Additional objects of the present invention will become apparent upon consideration of the following description of the present invention.

SUMMARY OF THE INVENTION

The present invention provides an improved intravenous catheter which may be easily inserted at a minimal diameter, but expanded once installed to a full operational diameter. The apparatus of the present invention comprises a first catheter tube member with an expandable overlapping sidewall, and a wider second member which is inserted to cause the first member to expand to its operational diameter.

Once the second member is inserted and the first member is fully expanded, the present invention may be employed with the second member providing a fluid conduit into the vein. Alternatively, by employing stops or locks on the first catheter tube member to force it to maintain its operational diameter once expanded, the second member may be removed once the first member is expanded and the first catheter tube member can provide the sole fluid conduit to the vein.

The present invention solves a long-standing problem of how to easily catheterize a patient while assuring that a catheter is provided on adequate diameter to provide all necessary medications. The present invention is particularly beneficial for catheterizing patients who are in shock or other trauma situations where his or her veins are significantly contracted.

The present invention integrates quite well with existing intravenous apparatus and requires minimal additional training and expense.

DESCRIPTION OF THE DRAWINGS

The operation of the present invention should become apparent from the following description when considered in conjunction with the accompanying drawings, in which:

FIG. 1 is an exploded three quarter view of one embodiment of a first catheter tube member of the present invention inserted in a vein and a second member adapted to be inserted therein;

FIG. 2 is a three quarter view of another embodiment of a first catheter tube member of the present invention with a second member inserted;

DETAILED DESCRIPTION OF THE INVENTION

The present invention provides an improved apparatus and method of employing an intravenous catheter. As is known, when a patient, either human or animal, is in a state of trauma or shock, his circulatory system contracts to reduce heat and blood loss. This autonomic response creates a major problem for emergency medical personnel who must attempt to catheterize a vein in the patient to provide necessary medication. The present invention provides means to insert easily a catheter of minimal diameter and then expand the diameter and fluid carrying capacity of the catheter once it is installed.

Figure 3:
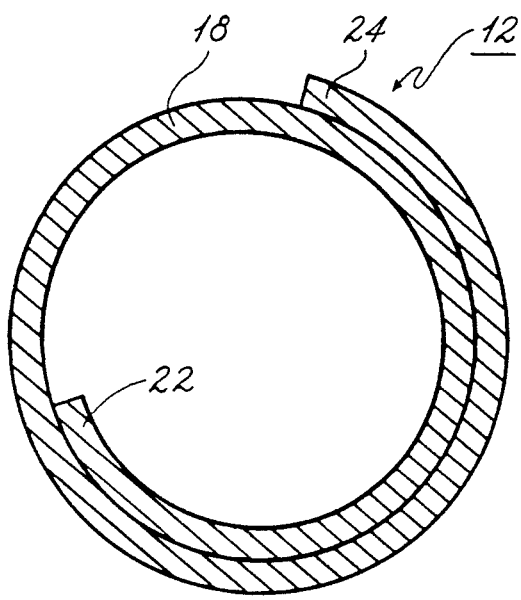
FIG. 3 is a cross-sectional view of the first catheter tube member of the present invention taken along line 3—3 of FIG. 1.

One embodiment of a catheter 10 of the present invention is shown in FIGS. 1 and 3. The catheter 10 shown comprises a first catheter tube member 12, which is inserted into a vein 14 in a manner described below, and a second tube member 16 adapted to be inserted into the first catheter tube member 12. When the first catheter tube member 12 is inserted it is in a contracted state, with its sidewall 18 substantially overlapping itself. In this manner, the first catheter tube member 12 may be inserted with an outside diameter of 20 gauge or less.

Once the first catheter tube member 12 is inserted in the vein 14, the second member 16 may then be inserted inside of it. The second member 16 has a diameter substantially larger than that of the first catheter tube 12 and its insertion causes the first catheter tube's sidewall 18 to expand, thus widening the opening into the vein 14. In the embodiment shown in FIG. 1, the second member 16 is a catheter tube with an substantially larger opening than that of the first catheter tube 12, providing a conduit into the vein of 18 to 14 gauge or greater. Once the second member 16 is installed, the medical technician need only attach the catheter in a conventional manner to a standard conduit (not shown) from a desired medication. It should be understood that the second member 16 may also be integral with the medication conduit so to provide one step attachment.

The sidewall 18 is preferably constructed from relatively stiff material which will tend to retain its initial coiled shape. In this respect, a plastic such as a thermoplastic, or other inorganic or organic polymer is believed to be suitable. The second tube member 16 may be constructed from any similar material, although silicone rubber or similar material may be preferred.

In order to allow the sidewall 18 to expand, it is attached at its base to a flexible catheter housing 20. The housing 20 is firmly attached to an inside edge 22 of the sidewall 18, but provides a loose, slidable fitting around the first catheter tube 12 to permit it outside edge 24 to move to permit expansion. Preferably, the housing 20 is constructed from an elastomer material, such as a silicone rubber or similar inorganic or organic polymer. Additionally, the housing 20 may be constructed from a non-elastic material which comprises the full operational diameter of the first catheter member 12. In this embodiment, the catheter 12 is expanded to meet the housing 20, with a seal formed between them upon expansion.

Although the sidewall 18 material will provide minimal bending, it is believed that flexibility should generally be avoided with the coiled first catheter tube member 12. Since it is sometimes desirable that the catheter be able to bend at some point along its length to permit adjustment of its location, a flexible joint may be provided along the length of the first catheter tube 12 constructed from a somewhat flexible material, such as an elastomer. Since bending of the stiff coiled sidewall 18 should be avoided, a wider section of solid flexible material may be provided near the housing 20 which will accommodate bending and still permit expanded flow.

Figure 4:
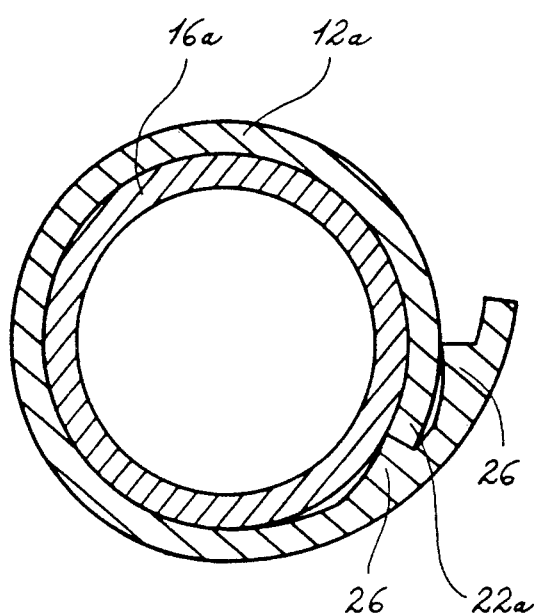
FIG. 4 is a cross-sectional view of the first catheter tube member of the present invention taken along line 4—4 of FIG. 2, showing one embodiment of locking means employed with the present invention.

A similar alternative embodiment of the present invention is shown in FIGS. 2 and 4. FIG. 2 shows the first catheter tube member 12a with the second member 16a inserted therein, providing expanded flow into vein 14. As is shown in FIG. 4, this embodiment additionally provides one-way stops 26 along the length of the first catheter tube 12, integral with the overlapped section of its sidewall 18. These one-way stops 26 permit the first catheter tube 12a to expand, but catch its inside edge 22a to prevent it from returning to its contracted state. Other means of preventing the first catheter tube member 12 from returning to its contracted state are shown in FIGS. 5 and 6.

Figure 5:
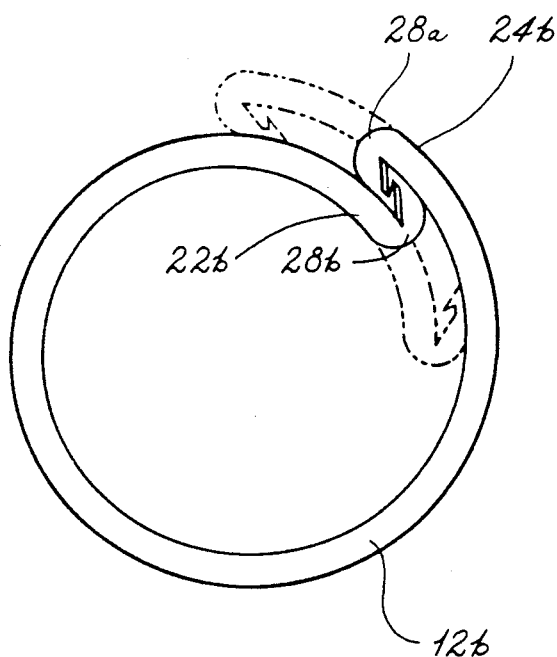
FIG. 5 is a cross-sectional view of another embodiment of the first catheter tube member of the present invention, showing another embodiment of locking means employed with the present invention.

The first catheter tube member 12b shown in FIG. 5 is provided with a hooked catch 28a, 28b on its outside edge 24b and its inside edge 22b, respectively. These catches 28a, 28b interlock upon one another both to prevent the first catheter tube 12b from expanding beyond itself, and to resist the first catheter tube 12b from returning to its contracted state.

Figure 6:
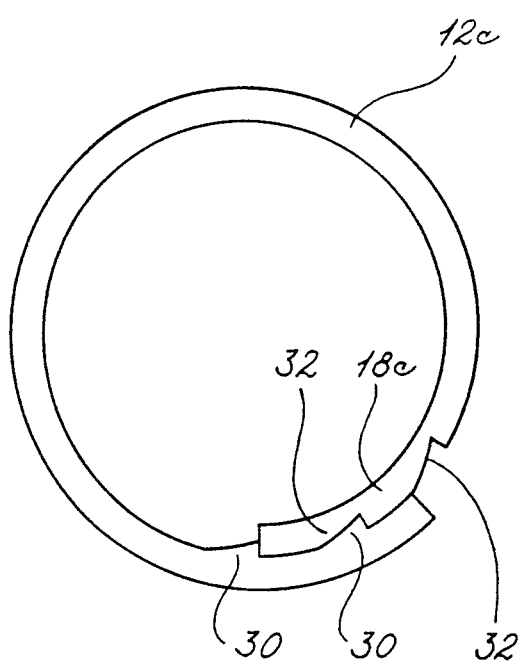
FIG. 6 is a cross-sectional view of another embodiment of the first catheter tube member of the present invention, showing yet another embodiment of locking means employed with the present invention.

The first catheter tube member 12c shown in FIG. 6 has one-way stops 30 similar to the ones employed in the embodiment of FIG. 4. However, notches 32 are also provided on the facing surface of the sidewall to provide a tighter fit between the overlapping portions of the sidewall 18c. It should be appreciated that other means of locking the first catheter tube member 12 in an expanded position may be employed without departing from the intent of the present invention.

By employing a lock or stop as discussed above, the present invention can be employed without the need of using the second member as a fluid conduit. When a lock or stop is utilized, the second member 16, which may be a solid rod or other suitable shape, may be inserted to expand the first catheter tube member 12 to its operational diameter, and then the second member 16 may be removed during use. This permits the first catheter tube member to serve as the sole conduit and it maximizes the amount of flow which can be achieved given a set outside diameter of the first catheter tube member 12.

Figure 7:
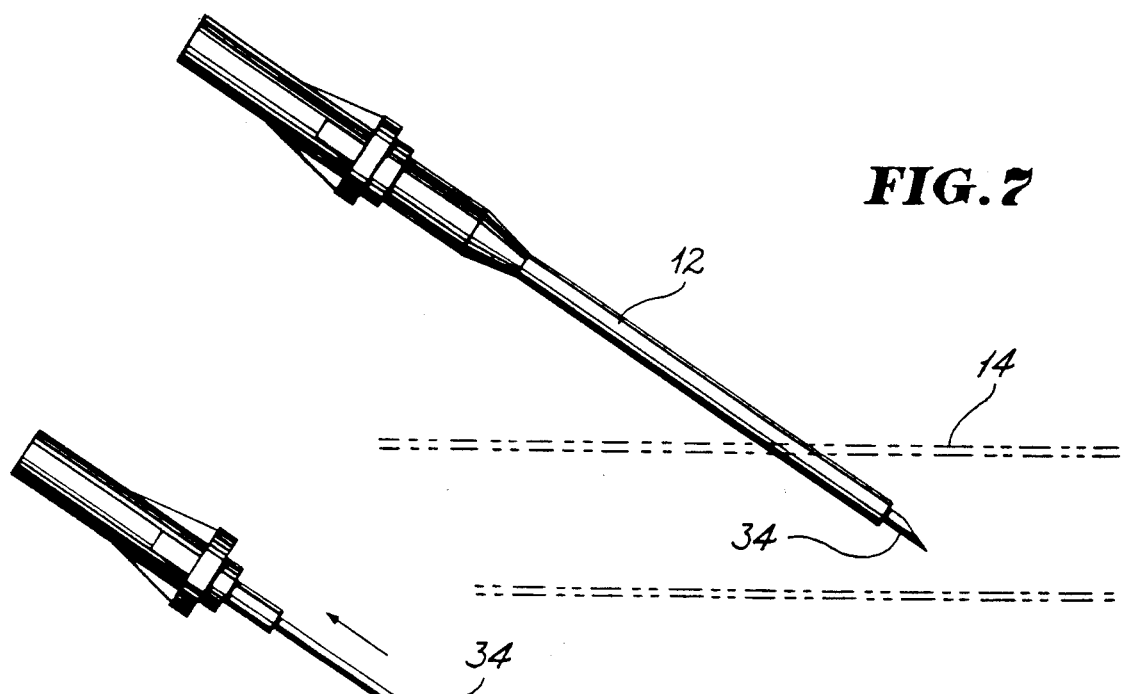
FIG. 7 is an elevational view showing one method of insertion of the first catheter tube member of the present invention, employing an insertion needle within the first catheter tube member.
Figure 8:
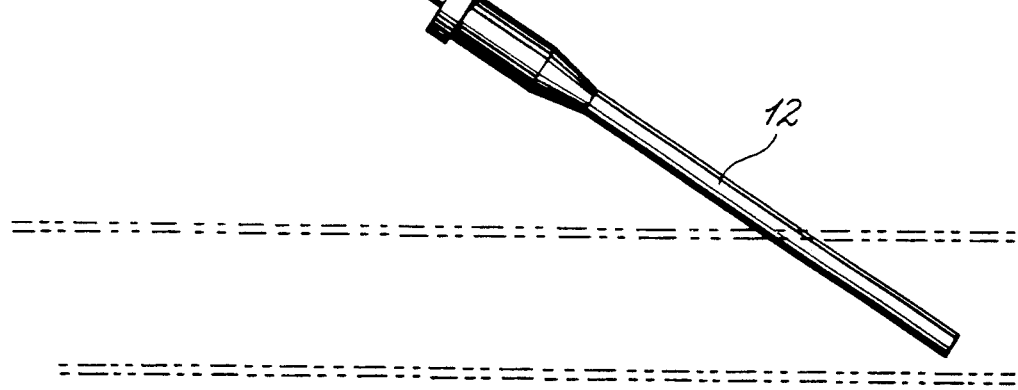
FIG. 8 is the elevational view of FIG. 7 showing the removal of the insertion needle.

FIGS. 7 and 8 demonstrate the method of inserting the catheter of the present invention. In order to install the first catheter tube member 12 into a vein 14, a needle 34 is first installed within the first catheter tube member 12. The needle 34 should be of minimum diameter so to provide ease in entering the vein and so not to expand the first catheter tube member 12 prior to installation. The first catheter tube member 12 is then installed in a conventional manner. The needle 34 is then withdrawn in the manner shown in FIG. 8. A second member 16 may then be inserted into the first catheter tube member 12 to cause it to expand in the manner described above. It should be understood that since the needle 34 need not serve as a fluid conduit in this application, it may take the form of a standard hypodermic needle or as a thin solid wire or other shape which will accurately pierce the skin and vein 14.

Figure 9:
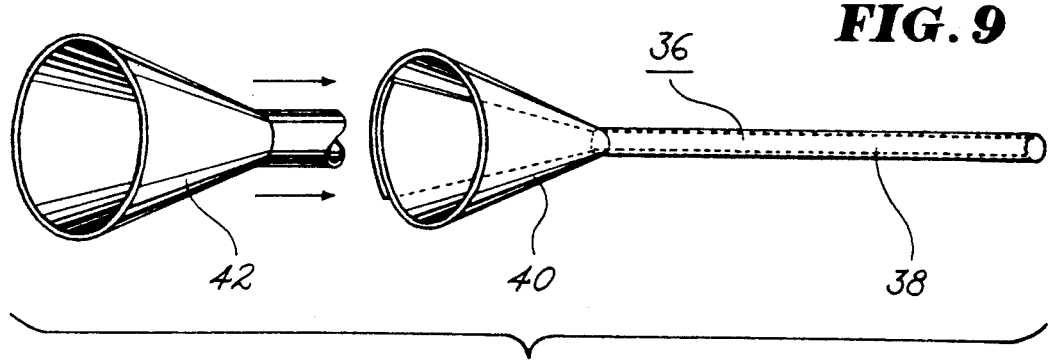
FIG. 9 is an exploded elevational view of another embodiment of the present invention.

FIG. 9 illustrates another embodiment of the present invention. In this embodiment a single unit 36 is provided comprising an expandable catheter member 38 integral with an expandable funnel-shaped housing 40. By providing locks or stops as described above on either or both of the catheter member 38 and expandable housing 40, the entire unit 36 may be accurately expanded and maintained in an operational state. The advantage of this embodiment is that it is believed to provide a better seal and it should be less prone to leakage.

A funnel-shaped second member 42, of uniformly wider diameter than the unit 36, may be employed to accurately expand the entire unit 36. Depending on the size of the catheter member 38 and the choice of materials, it may be possible to truncate the second member 42 so that it need not be inserted fully into the catheter member 38 in order to fully expand the unit 36. However, it should be evident that a full length second member 42 may be employed, with or without stops on the unit 36, in the manner shown in FIG. 1 to provide an even better sealed catheter unit.

Figure 10:
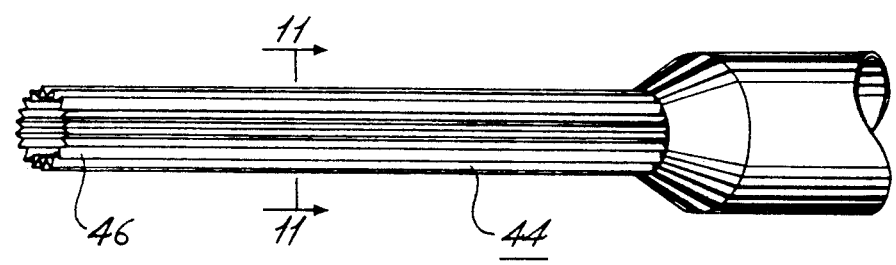
FIG. 10 is an elevational view of another embodiment of the present invention.
Figure 11:
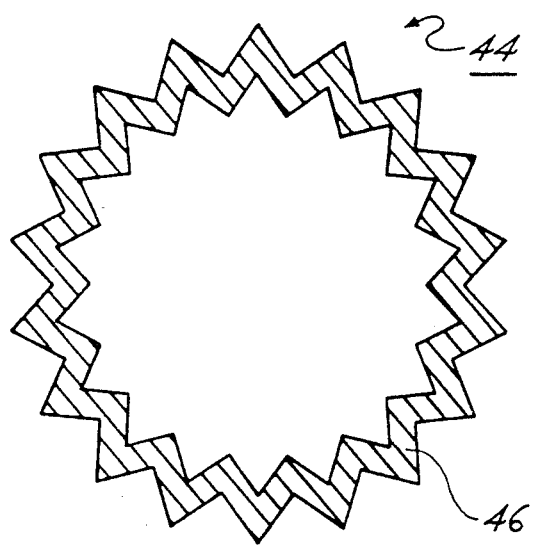
FIG. 11 is a cross-sectional view taken along line 11—11 of FIG. 10.
Figure 12:
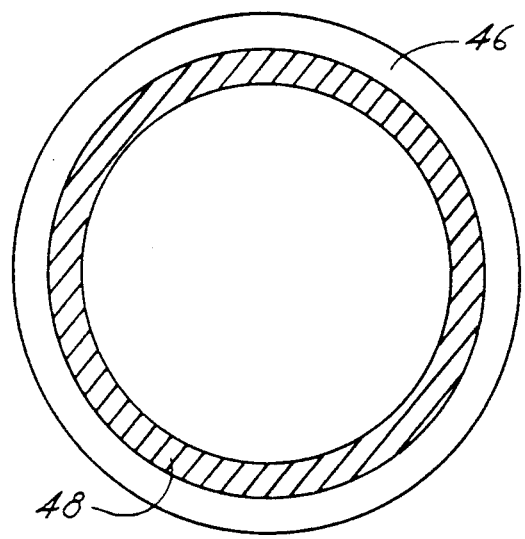
FIG. 12 is a cross-sectional view of the embodiment of the present invention shown in FIG. 11 with a second member inserted and the first catheter tube member shown fully expanded.

FIGS. 10 and 11 show another means of providing overlap of a first catheter tube member 44. In this instance, the first catheter tube member 44 is provided with bellows pleated sidewall 46 on part or all of its circumference. This embodiment provides the necessary overlap of the sidewall 46 to permit expansion, but avoids any opening, as is the case with a coiled overlap described above, which may cause bending problems and possible leakage. Although a pleated sidewall 46 generally is not desirable for insertion into a vein since leakage may occur around the pleats, as is shown in FIG. 12, once the sidewall 46 is expanded with the insertion of a second member 48, a smooth circumference is then provided.

It should be clear that other means of providing overlap of the first catheter tube member may be provided without departing from the intent of the present invention. Other means of providing overlap, and of possibly limiting leakage, may include: a two-part first catheter tube member, with a coiled inner conduit and a coiled outer conduit positioned coaxially, which complements itself to avoid leakage; and a first catheter tube member with a sealed elastomer sidewall which will expand upon insertion of a second member.

Figure 13:
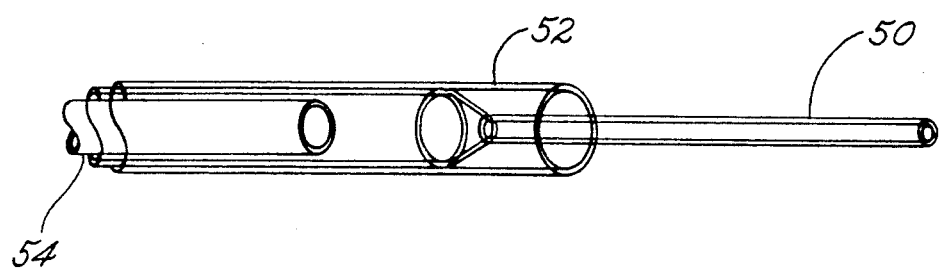
FIG. 13 is an elevational view of another embodiment of the present invention.

Shown in FIG. 13 is another embodiment for carrying out the present invention. In this embodiment the catheter tube 50 is constructed from a seamless length of expandable material. The catheter 50 is attached at its distal end to a wider sleeve 52. A second member 54 is provided which is inserted into the catheter tube in the manner described above.

Ideally the catheter tube 50 should be constructed from an expandable flexible material which expands over its entire length when enlarged at the end joined to sleeve 52. In this manner, the second member 54 need not be fully inserted into the catheter 50 to provide full length expansion. It is believed that Arbosol PVC tubing, such as that sold under the trademark Plastisol by Arbonite of Doylestown, Pa., will function well in this application.

The advantage of this form of the present invention is that no seams or pleats exist along the length of the catheter which may lead to leakage. Although a catheter of flexible material may not readily lock into an expanded position, this form of the invention is believed to be quite beneficial through the use of a partial or full length second member 54.

Other modifications can be provided to the present invention which may expand its usefulness. Among these are the beveling of the interior to the catheter, with corresponding modification to the remainder of the unit, to ease its insertion and improve its operation. Additionally, for some applications the second member 16 may be beveled at its end to aid in its insertion. Further, the present invention may be employed for the insertion of through-the-needle type catheters. Presently the use of such catheters is limited to the size of the needle which is initially inserted. For example, a 20 gauge needle can only handle the insertion of a 21 or 22 gauge catheter. By employing an expandable catheter of the present invention, any size initial needle can be used. Once the expanded catheter is installed and expanded, virtually any size of through-the-needle type catheter can then be inserted. This embodiment of the present invention has the added advantage that the expanded catheter can then be removed and the possibility of leakage or clotting is greatly reduced.

The present invention provides many important benefits over existing intravenous catheterization techniques. First and foremost, the present invention provides easy and straightforward means to catheterize all forms of patients, including ones in severe trauma. In this respect, the present invention may be quite useful for both human and veterinary medicine, and especially for emergency medicine. Additionally, the present invention may be used for normal catheterization applications. By employing a catheter of the present invention in non-trauma situations, it provides both ease of insertion and a previously unavailable option for the medical personnel to increase the size of the catheter without having to re-catheterize the patient.

While particular embodiments of the present invention have been illustrated and described herein, the present invention should not be limited to such illustrations and description. It should be apparent that changes and modifications may be incorporated and embodied as part of the present invention within the scope of the following claims.

What is claimed is:

1. An apparatus for inserting a catheter into a vein and expanding the catheter's fluid carrying capacity once inserted which comprises:

a first catheter tube member including means to increase its cross-sectional diameter from a contracted insertion diameter to an expanded operational diameter;

means to retain the first catheter tube member at its operational diameter;

a second member adapted to insert into and expand the first catheter tube member, the second member having a cross-sectional diameter substantially greater than the diameter of the first catheter tube member;

the means to increase the cross-sectional diameter of the first catheter tube member comprising a sidewall of the first catheter tube member which substantially overlaps itself when in its contracted state;

the means to retain the first catheter tube member at its operational diameter comprising a one-way stop which permits it to expand while resisting return to its contracted state;

wherein the first catheter tube member is inserted into the vein in its contracted state and the second member is then inserted into the first catheter tube member causing it to expand to its operational diameter.

2. The apparatus of claim 1 wherein the second member is a catheter tube and fluid flows into the vein through the second member.

3. The apparatus of claim 1 wherein fluid flows into the vein through the first catheter tube member.

4. The apparatus of claim 1 wherein the means to retain the first catheter tube member at its operational diameter comprises a series of one-way stops placed longitudinally along the length of the first catheter tube member which permit the first catheter tube member to expand while resisting the return of the first catheter tube member to its contracted state.

5. The apparatus of claim 4 wherein the overlapping portion of the first catheter tube member has an interior section and an exterior section and the one-way stops comprise corresponding angled teeth on the interior and exterior sections of the overlapping portion which interlock with one another to prevent the first catheter tube member from returning to a contracted state.

6. The apparatus of claim 1 wherein the first catheter tube member comprises a resilient material coiled along its longitudinal axis.

7. The apparatus of claim 6 wherein the first catheter tube member is coiled to provide at least a fifty percent overlap when the first catheter tube member is in its contracted state.

8. A method of catheterizing a patient to permit increased fluid flow into the patient which comprises:

providing a first catheter tube member including means to expand its diameter from a contracted insertion diameter to an expanded operational diameter to increase the capacity of the fluid which can flow therethrough, such means to expand the diameter of the first catheter tube member including providing the first catheter tube member with a sidewall which substantially overlaps itself in its contracted state and locking means on the sidewall of the first catheter tube member to maintain it in an expanded state;

inserting the first catheter tube member at a contracted diameter into a patient's vein;

inserting a second member into the first catheter tube member to cause the first catheter tube member to expand to its operational diameter; and providing fluid to the patient through the first catheter tube member.

9. The method of claim 8 wherein the second member is hollow and remains inserted in the first catheter tube member during use, the fluid being provided to the patient through the second member.

10. The method of claim 8 wherein the second member is removed from the first catheter tube member after it is expanded to an operational diameter.

11. The method of claim 8 wherein the first catheter tube member is inserted into the patient's vein by first inserting a needle into the first catheter tube member in its contracted state, inserting the needle and the contracted first catheter tube member into the vein, and then removing the needle.

12. An apparatus for inserting a catheter into a vein and expanding the catheter's fluid carrying capacity once inserted which comprises:

a first catheter tube member including means to increase its cross-sectional diameter from a contracted insertion diameter to an expanded operational diameter;

a second member adapted to insert into and expand the first catheter tube member, the second member having a cross-sectional diameter substantially greater than the insertion diameter of the first catheter tube member;

the means to increase the cross-sectional diameter of the first catheter tube member comprising an elastic sidewall of the first catheter tube member which is capable of increasing substantially in diameter from a contracted state to an expanded operational state;

wherein the first catheter tube member is inserted into the vein in its contracted state and the second member is then inserted into the first catheter tube member causing it to expand to its operational diameter; and wherein the first member is constructed from material which expands over its entire length when expanded at its proximal end, and the second member comprises a shortened tube of greater diameter than the contracted diameter of the first member, the insertion of the second member into the proximal end of the first member causing the first member to expand to its operational diameter along its entire length.

13. The apparatus of claim 12 wherein the second member is a catheter tube and fluid flows into the vein through the second member.

* * * * *